United States Patent [19]
Wilkins

[11] Patent Number: 5,431,160
[45] Date of Patent: Jul. 11, 1995

[54] MINIATURE IMPLANTABLE REFILLABLE GLUCOSE SENSOR AND MATERIAL THEREFOR

[75] Inventor: Ebtisam S. Wilkins, Albuquerque, N. Mex.

[73] Assignee: University of New Mexico, Albuquerque, N. Mex.

[21] Appl. No.: 150,948

[22] Filed: Nov. 9, 1993

Related U.S. Application Data

[60] Continuation-in-part of Ser. No. 600,546, Oct. 18, 1990, abandoned, which is a division of Ser. No. 382,603, Jul. 19, 1989, Pat. No. 4,986,271.

[51] Int. Cl.6 ............................................. A61B 5/00
[52] U.S. Cl. ...................................... 128/635; 204/403; 204/415; 435/12; 435/14; 435/177; 435/817
[58] Field of Search ................. 128/632, 635, 637; 435/817, 4, 12, 14, 174, 176, 177, 182; 204/403, 415; 436/535, 808

[56] References Cited

U.S. PATENT DOCUMENTS

| | | |
|---|---|---|
| 3,979,274 | 9/1976 | Newman . |
| 4,224,125 | 9/1980 | Nakamura et al. . |
| 4,240,438 | 12/1980 | Updike et al. . |
| 4,376,689 | 3/1983 | Nakamura et al. . |
| 4,418,148 | 11/1983 | Oberhardt . |
| 4,655,880 | 4/1987 | Liu . |
| 4,703,756 | 11/1987 | Gough et al. . |
| 4,986,271 | 1/1991 | Wilkins .......................... 128/635 |
| 5,250,419 | 10/1993 | Bernard et al. ............... 128/635 |
| 5,272,087 | 12/1993 | El Murr et al. ............... 435/177 |

FOREIGN PATENT DOCUMENTS 9219150  11/1992  European Pat. Off. ............ 128/632

Primary Examiner—Krista M. Pfaffle
Attorney, Agent, or Firm—Robert Becker

[57] ABSTRACT

A reusable, miniature, implantable electrochemical sensor, a method of making the same, and a powder therefor are provided. Enzyme material is immobilized on bulk particulate matter, and a reaction chamber of the sensor is then filled therewith. The sensor is implanted in an environment where it comes into contact with a specific component of a fluid with which the enzyme material chemically reacts to produce electrical signals for measuring the reaction.

10 Claims, 4 Drawing Sheets

MINIATURE IMPLANTABLE REFILLABLE GLUCOSE SENSOR AND MATERIAL THEREFOR

This application is a continuation-in-part application of Ser. No. 07/600,546, filed Oct. 18, 1990, now abandoned, which in turn is a divisional application of Ser. No. 07/382,603, filed Jul. 19, 1989, now U.S. Pat. No. 4,986,271.

FIELD OF INVENTION

This invention, for example a glucose sensor, relates to a reusable miniature implantable sensor employing an enzyme such as glucose oxidase immobilized on a bulk powder such as very fine graphite or carbon particles. The sensor is small enough to be inserted into human or animal tissues or blood streams either directly or via a catheter, and has a lifetime of stable and reliable operation long enough for up to several weeks. The enzyme immobilized on fine particles can be removed from the sensor after its use or when exhausted and replaced by fresh enzyme-loaded particles, thereby prolonging the useful life of the sensor.

This invention also relates to a refillable implantable glucose sensor employing an enzyme such as glucose oxidase immobilized on a bulk powder such as very fine graphite particles which can be exhausted from the implanted sensor when spent and replaced by fresh enzyme-loaded particles, thereby prolonging the useful life of the implanted sensor without the need for surgery.

BACKGROUND OF THE INVENTION

Glucose sensors of the type employing enzymes are well known. Many of these feature an "enzyme electrode" which consists of an immobilized enzyme such as glucose oxidase that catalyzes a chemical reaction involving glucose and oxygen—a reaction that involves the catalytic conversion of glucose to gluconic acid and hydrogen peroxide with simultaneous consumption of oxygen. The resulting decrease in consumption of oxygen may be measured by a current sensitive oxygen electrode. The production of hydrogen peroxide can also produce a current to be measured by a hydrogen peroxide electrode. Various arrangements for glucose sensors are described in the following U.S. Patents: U.S. Pat. No. 4,703,756 which utilizes first and second tandem sensor elements mounted in a catheter, one of which sensors acts as a reference and the other of which contacts glucose oxidase, whereby an electrical signal is produced indicative of the oxygen content differential between the two sensors; U.S. Pat. No. 4,240,438 which uses a hydrophobic membrane on which the glucose oxidase is immobilized and which senses the rate of oxygen consumption by the glucose contained in the blood; U.S. Pat. No. 4,655,880 which provides a multiple electrode sensor for measurement of glucose concentration by comparing electron current flow in working and counter electrodes in relation to current flow in a reference electrode; U.S. Pat. No. 3,979,274 which utilizes a laminated enzyme electrode with special filtering properties thereby eliminating the need for a compensating or reference electrode; U.S. Pat. No. 4,224,125 which has an enzyme electrode using an oxidoreductase and a redox copolymer acting as an electron mediator in an enzymatic reaction maintained in an immobilized state on an electron collector or semipermeable membrane; U.S. Pat. No. 4,376,689 wherein the coenzyme is immobilized directly on an electron collector (eliminating the need for a membrane) whereby the activity of the enzyme on a substrate can be directly measured; U.S. Pat. No. 4,418,148 employing a contiguous multilayer membrane structure enabling a more homogeneous distribution of enzyme.

At present there does not exist an enzyme type glucose sensor of small enough size to allow insertion directly into blood streams or tissue either directly or via a catheter, which contains a reservoir filled with enzyme immobilized on a powder so as to provide an extended operational lifetime and providing for reuse by refilling.

The inventive miniature glucose sensor can be used to provide continuous monitoring of blood glucose levels in trauma patients suffering from hemorrhagic shock. This will enhance the medical management of such patients in the field, while being transported, and in the hospital, thus increasing survival rates.

SUMMARY OF THE INVENTION

The present invention provides an improved arrangement for an implantable electrochemical sensor such as a glucose sensor of the type in which the enzyme material degrades due to reaction with components of bodily fluids, the improvements being that degraded enzyme material can be replaced with fresh enzyme material, and that it is of small enough size to be inserted directly or via a catheter into tissues or blood streams, or is of small enough size to allow for incorporation into a catheter assembly, thus prolonging the useful implanted life of the sensor.

According to one embodiment of the present invention there is provided a bulk powder of fine particles carrying immobilized enzyme material. The bulk powder is carried as a suspension in a gel cross-linked matrix. The sensor is constructed so as to allow the sensor to be removed, disassembled, cleaned, and recharged. The sensor has been miniaturized to fit into a 6 or smaller (down to 32) gauge tube or needle.

The sensor has a housing or body defining an outer chamber bounded at its working end, or on the side, by an outer, hydrophilic or hydrophobic membrane which enables bodily fluids to interact with a cathode. The outer membrane is adjacent to the platinum anode. The membrane passes molecules such as glucose but not large molecules of bodily fluids. The reservoir contains powder which comprises enzyme material such as glucose oxidase material immobilized on particles of the bulk powder, which is in a gelled matrix. The glucose oxidase reacts with the incoming glucose to deplete oxygen, and produce hydrogen peroxide; this is sensed by the anode to detect the amount of glucose.

Also, in accordance with another embodiment of the invention, the stability of the enzyme material may be further improved by providing in the sensor an additional replenishable enzyme such as catalase also immobilized on particles of bulk powder carried in a gel. The catalase material removes and neutralizes the hydrogen peroxide produced by the reaction of glucose with glucose oxidase, and in this embodiment the sensor will operate as an oxygen sensor measuring oxygen, instead of hydrogen peroxide. The anode and cathode are each electrically coupled to signal processing and monitoring circuitry positioned outside the body.

BRIEF DESCRIPTION OF THE DRAWINGS

Reference is now made to the accompanying drawings in which like numerals represent like parts and in which.

DETAILED DESCRIPTION OF THE INVENTION

Figure 1:
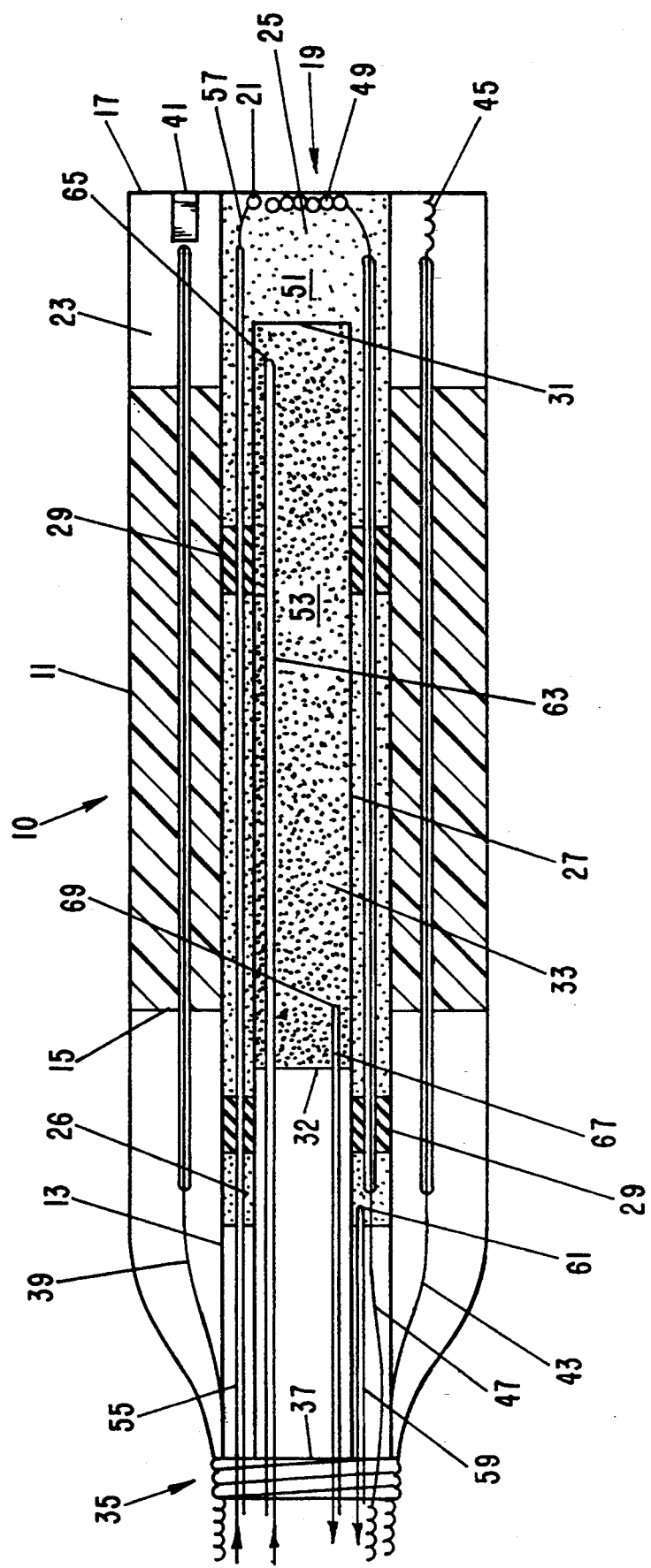
FIG. 1 is a cutaway view in longitudinal cross section of a glucose sensor in accordance with an embodiment of the invention.

According to the embodiment of the invention shown in FIG. 1, a glucose sensor 10 in accordance with the principles of the invention has a generally cylindrical housing 11 of any suitable inert material which does not deleteriously react with bodily fluids or tissue. Located within the housing 11 is a generally cylindrical inner housing 13 of like inert material supported in spaced apart relation from the housing 11 by an annular member 15, also of inert material. An outer membrane 17 made of any suitable well-known hydrophilic material spans the extent of one end of the housing 11, hereinafter referred to as the working end 19 of sensor 10.

An inner membrane 21 made of any suitable well-known hydrophobic material covers the working end of the inner housing 13. The inner membrane 21 underlies the outer membrane 17. Consequently, the spaced apart housings 11 and 13 together with their respective membranes 17 and 21 define an outer annular reaction chamber 23 and an inner reaction chamber 25 concentric therewith. The inner chamber 25 is effectively enclosed or bounded at its working end by both the membrane 17 and 21 and at its other end by a fluidtight transverse wall 26.

Also, according to an embodiment of the invention there may be provided a central housing 27 located within the inner housing 13 and held in spaced apart relation therefrom by annular spacers 29. The spacers 29 may be in the form of spoked rings of inert material so that enzyme material may easily pass longitudinally back and forth therethrough in the chamber 25. The central housing 27 has a hydrophobic membrane 31 at the sensor's working end 19 spaced apart from the membrane 21 and at its other end a transverse wall 32. The housing 27, wall 32, and membrane 31 define a central chamber 33.

The other end of the sensor 10, referred to hereinafter as the feed end 35 for purposes of convenience, has a fluid tight seal 37 made of any suitable well-known material non-reactive with bodily fluids. The seal 37 defines the closed other end of the outer annular reaction chamber 23 and can, if desired, be used in place of transverse walls 26 and 32 to define the closed end of the inner chamber 25 and the central chamber 33.

An insulated, electrically conducting lead 39 passes fluidtightly through the seal 37 and extends longitudinally through the spacer member 15 into chamber 23. A reference electrode 41 composed of both silver and silver chloride is electrically connected to the lead 39 in the chamber 23. The reference electrode 41 may be immediately adjacent to or in intimate physical contact with the outer membrane 17.

Another insulated electrically conducting lead 43 passes fluidtightly through the seal 37 and longitudinally through the spacer member 15 and terminates in the outer annular chamber 23 at a cathode or counter electrode 45 made of any suitable noble metal in the form of a helix or mesh or other suitable configuration to provide a large area of reaction located adjacent to or in intimate physical contact with the outer membrane 17. A third insulated electrical lead 47 passes through the seal 37 and terminates in the inner chamber 25 at a helical platinum anode or working electrode 49 immediately adjacent to or in intimate physical contact with the inner membrane 21.

The outer membrane 17 is of any suitable well-known material to permit the passage of bodily fluids therethrough into the chamber 23. Membrane 17 prevents the entry of large proteins or other large molecules or particulate matter into the chamber 23. The hydrophobic inner membrane 21 operates through molecular diffusion and is of any suitable well known material to enable the passage therethrough into the chamber 25 of only small molecules including limited amounts of glucose which may be present in bodily fluids. Water, large molecules, and large amounts of glucose are excluded by the membrane 21.

The inner chamber 25 is filled with the enzyme material such as glucose oxidase immobilized on and bonded to, i.e., fixed to, bulk powder material which is preferably electrically conductive and may comprise very fine particles of graphite, indicated by the numeral 51. Alternatively, the material 51 may be constituted of very fine particles of nylon, polyethylene, polystyrene, or electrically conducting polymers. The response or reaction time of the enzymes is advantageously somewhat shorter where the enzymes are carried on particles, especially electrically conductive particles, such as graphite. This reaction time is longer where the enzymes are fixed as in the prior art, on probes, rods, or membranes. This is due to the movement of the particles and the better contact because of the small size and the electrical conductivity of the particles. The central chamber is filled with a catalase enzyme material generally indicated by the numeral 53. The catalase enzyme material is also immobilized and bonded, i.e., fixed, to very fine particles of graphite in the same manner as the glucose oxidase.

The glucose oxidase enzyme material 51 for chamber 25 may be prepared as set forth in the following Example 1.

EXAMPLE

[a] Add 10 mg of glucose oxidase to 42.5 Bovine Serum Albumin and 0.19 ml of 2.5% Gluteraldehyde to provide a cross-linked enzyme;

[b] To provide covalent linking of the glucose oxidase on modified graphite [i.e., glucose oxidase immobilized on the particles], [1] add 2 g of fine graphite powder about 44 microns in diameter or less particle size to 0.15M 1-cyclohexl-3-(2)morpholinoethyl, carbodiimide, metho-p-toluene sulfonate in 5 ml of 0.1M acetate buffer pH 4.5 at 20 degrees centigrade for 2 hours, [2] wash thoroughly with distilled water, then add 2 ml of 10 mg/ml glucose oxidase in 0.1M acetate buffer pH 4.5 at 4 degrees C. for 3 hours, and [3] wash with distilled water and dry in room temperature air; store the dry powder in refrigerator;

[c] Add 120 mg of the immobilized glucose oxidase produced as in [b] above to the cross linked enzyme produced in [a] above.

The catalase 53 for chamber 33 is produced as follows:

[d] Add 1.8 mg catalase to 42.5 mg Bovine Serum Albumin and 0.19 ml of 2.5% Gluteraldehyde;

[e] Add 120 mg of fine graphite powder with catalase immobilized thereon in the same manner as described in [b] above for glucose oxidase. [End of Example.]

Also extending fluidtightly through the seal 37 is an injection or charge tube 55 for introducing fresh enzyme material such as glucose oxidase into the inner chamber 25. The tube 55 terminates in an opening 57 located in the inner chamber 25 near the inner membrane 21. A discharge or exhaust tube 59 for expelling spent enzyme material from the chamber 25 has its opening 61 located near the feed end 35 of the sensor.

A catalase enzyme charge tube 63 passes fluidtightly through the seal 37 into the central chamber 33 and has its open end 65 near the membrane 31. A catalase discharge or exhaust tube 67 also passes fluidtightly through the seal 37 into the central chamber 33 and has its open end 69 near the feed end 35 of the sensor and thus, its open end is relatively remote from the membrane 31. As is well known in the art, the catalase enzyme serves to decompose hydrogen peroxide generated by the oxidation of the glucose occurring in the inner chamber 25. This prolongs the useful life of the glucose oxidase.

Figure 2:
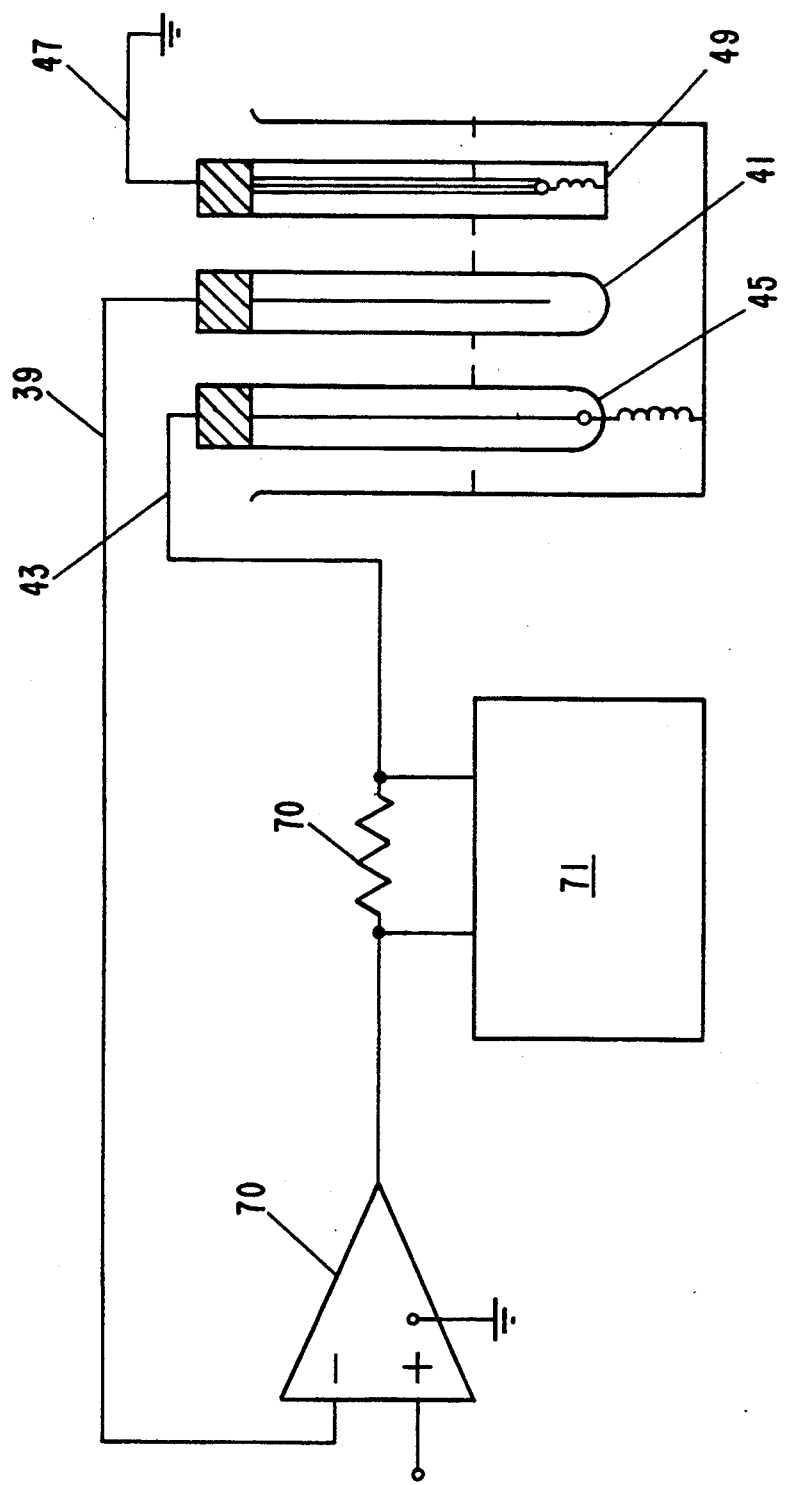
FIG. 2 is a schematic circuit diagram of an arrangement for indicating readouts of glucose concentrations in accordance with an embodiment of the invention.

Referring to FIG. 2, the leads 39, 43, and 47 for the respective electrodes—reference electrode 41, the counter electrode or cathode 45, and the working electrode or anode 49—are connected as inputs to a potentiostat amplifier 70. Such an amplifier and the connections thereto for an enzyme glucose sensor are well known in the art such as in aforementioned U.S. Pat. No. 4,703,756 and will not be described in detail. The working electrode or anode 49 puts out an electrical current having an amplitude proportional to the chemical process catalyzed by the sensor attached to it. In particular, the chemical process involved here is very well known in the art and is characterized by the decrease in oxygen and production of hydrogen peroxide resulting from the oxidation of glucose caused by reaction of the glucose with the enzyme material in inner chamber 25.

In a manner that is well known in the art, the working electrode or anode 49 provides a current having an amplitude proportional to the above-mentioned oxidation of glucose. The reference electrode 41 provides a calibrated reference voltage for the operation of the potentiostat amplifier 70. The cathode or counter electrode 45 provides a return path corresponding to the ground connection of amplifier 70. The current appearing on lead 47 is converted to a voltage proportional to such current by the amplifier 70, as is indicated by a voltage dropping resistance 70a across which may be connected a suitable monitoring or readout device such as a voltmeter 71. Of course, in a manner well known in the art, device 71 may be a voltage-controlled telemetering unit for transmitting a signal to a remote location such as a central monitoring station or may be any other suitable utilization device, such as a monitoring device attached to a patient.

Figure 3:
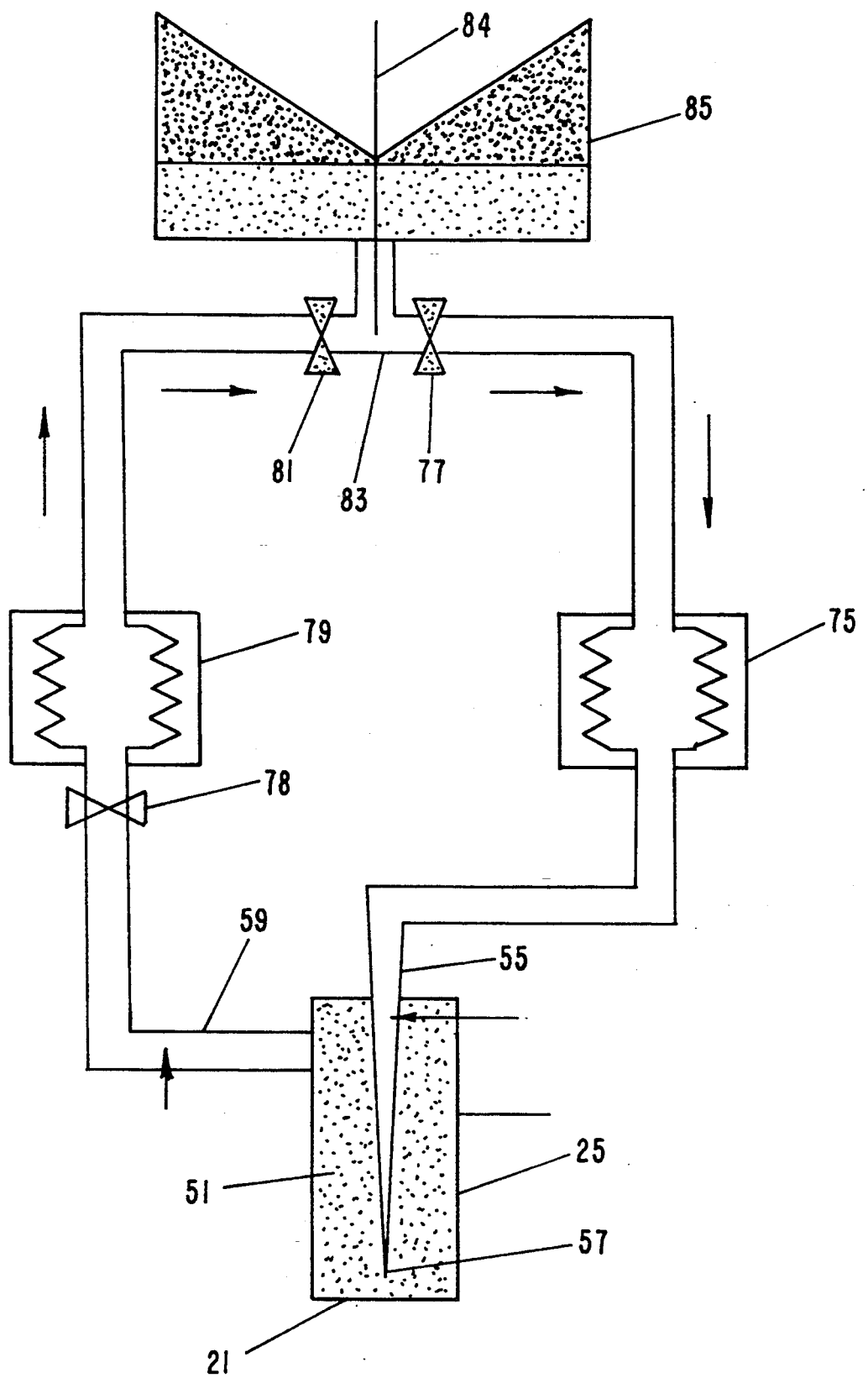
FIG. 3 is a schematic diagram of a recharging and discharging arrangement for replenishing spent enzyme material in accordance with an embodiment of the present invention.

Referring to FIG. 3, a charge tube or line 55 and discharge or exhaust tube or line 59 for respectively replenishing and exhausting the enzyme material 51 in chamber 25 are shown in a replenishment system according to an embodiment of the invention. This system may also be used for handling recharging and expelling of the catalase enzyme material 53 located in chamber 33 via tubes 63 and 69. Upstream from the feed end of the charge tube 55 is a reservoir 75 which may comprise a bellows and a one-way valve 77 of any suitable well known construction. A first valve 78 in the discharge line 59 and a reservoir 79 which also may be of the bellows type located downstream of the feed end of the discharge tube 59 for handling the spent enzyme material. A second one-way discharge valve 81 is located downstream of the reservoir 79. All of these elements may be implanted preferably near the sensor.

As further shown in FIG. 3, the charge and discharge tubes 55 and 59 converge at a junction 83 immediately adjacent valves 77 and 81 for transcutaneous reception of a needle or plurality of needles 84 via needle guide 85 of any suitable well known construction.

The procedure for charging and discharging the enzyme material will now be explained. It should be understood that the same procedure applies to handling of both the glucose oxidase in chamber 25 and the catalase in chamber 33. When the enzyme material such as the glucose oxidase is spent or degraded after use, a needle is inserted in the guide 85 to deliver fresh enzyme material to the reservoir 75. The reservoirs 75 and 79 as well as the rest of the fluid handling system including the tubes 55 and 59 are at essentially atmospheric pressure. The enzyme material, for example, glucose oxidase immobilized on fine particles of graphite suspended in the fluid described above, enters the charge reservoir 75 thereby forcing the material therein to flow through tube 55 and from opening 57 into the inner chamber 25 of sensor 10. The slight differential in pressure caused by the injection of the fresh material causes the spent material to exit chamber 25 at the feed end 35 via opening 61 of the discharge tube 59 and flow via one-way valve 78 into the discharge reservoir 79. The one-way valve 78 prevents the spent material from backing into the chamber 25.

Because the opening of tube 55 is proximate the region of the working end of the sensor near the membrane 21 and the electrode 49 in chamber 25, during replenishment the fresh enzyme material tends to be concentrated in that region where it can interact with the incoming glucose while the spent enzyme material tends to move away from that region through the opening 61 of discharge tube 59 at the feed end 35 of the sensor. When the discharge reservoir 79 becomes full, an additional needle is employed via the needle guide 85 to exhaust the spent material from the reservoir 79 at substantially the same rate the fresh material is injected into the charge reservoir 75. If desired, two needles may be used simultaneously, one for injecting fresh material and one for exhaust the spent material.

As stated previously, the recharging of the catalase material works in exactly the same way as described above for the glucose oxidase, the replenishment arrangement of FIG. 2 providing recharging of catalase via tube 63 and exhaust via tube 67 in the same manner as for respective tubes 55 and 59.

In accordance with another embodiment of the invention, the catalase enzyme material need not be employed, and thus, referring again to FIG. 1, the central housing 27 and its associated elements, the membrane 31 and the tubes 63 and 67 may be eliminated. Consequently, in accordance with this embodiment, there is provided only an outer chamber 23 and an inner chamber 25 defined by respective housings 11 and 13 and the membranes 17 and 21. Advantageously, in this embodiment the glucose oxidase enzyme material is preferably prepared as set forth in the following Example 2.

EXAMPLE 2

[1] Add 10 mg of glucose oxidase activity (50,000 units/0/29 g) to 42.5 mg of Bovine Serum Albumin (Sigma), and dissolve in 0.24 ml distilled water, then 0.55 ml phosphate buffer pH 7.4.;

[2] add 0.18 ml (2.5%) Glutaraldehyde, the solution being kept in a high moisture content atmosphere for 60 minutes, and then left overnight for cross linking to take place;

[3] Provide covalent linking of the glucose oxidase on modified graphite powder in accordance with the procedure set forth in [b] above; and

[4] Add 120 mg of the immobilized glucose oxidase produced in [3] above to the cross linked enzyme produced from steps [1] and [2] above. [End of Example.]

Indications from tests employing apparatus constructed substantially in accordance with an embodiment of the invention show sustained responsiveness of the sensor to variations in glucose over a continuous four-months period. This indicates that the use of bulk amounts of immobilized and/or cross linked enzyme greatly extends the life of the sensor and thus extends the period before refill is needed.

Further, the rechargeable glucose sensor of the present invention provides these important advantages:

[i] continuous monitoring of glucose concentration;

[ii] long life time of several years afforded through recharging;

[iii] small applied voltage;

[iv] immobilization of enzymes on bulk particulate matter enabling efficient reaction with glucose and accurate measurement on a linear basis of glucose levels.

Figure 4:
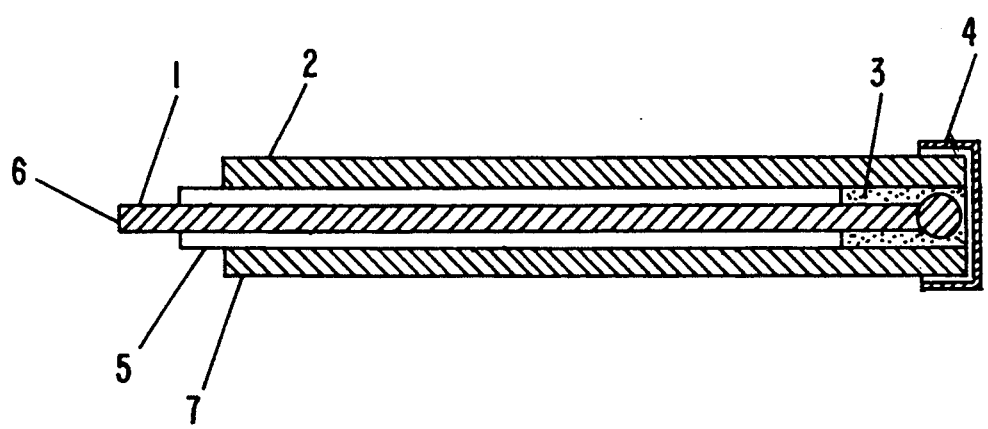
FIG. 4 is a cutaway view in longitudinal cross section of a further glucose sensor in accordance with an embodiment of the invention.

A preferred embodiment of the miniaturized version of the inventive sensor is shown in FIG. 4. Such a sensor can be of the size of a tube or needle of 6 gauge or smaller, for example down to 32 gauge. In the two electrode prototypical system illustrated in FIG. 4, a platinum wire, which in this embodiment has a diameter of about 0.25 mm, but can be larger or smaller, forms the anode 1. The stainless steel body of the needle serves as the cathode 2. It should be noted that as an alternative the cathode body 2 can be of some other metal, either by itself or plated with Ag/AgCl. The annular cavity that is provided between the two electrodes 1, 2 constitutes a reservoir that is filled at least partially, although preferably entirely, with the gelled immobilized glucose oxidase enzyme or some other enzyme immobilized on fine carbon or graphite powder; this immobilized enzyme gel is indicated by the reference numeral 3. A glucose diffusion membrane 4, which is hydrophilic or hydrophobic, is attached to the needle either on the open end as shown in FIG. 4 or over a hole in the side of the needle. The sensor electrodes 1, 2 are electrically insulated from one another by an insulating material 5, such as a polymer, glass, plastic, etc. The overall diameter of the biosensor can range from 5.2 mm to 0.10 mm, and the length thereof can range from 40 mm down to about 10 mm.

The anode and cathode leads or wires 6 and 7 are led by suitable wiring to electronic circuitry that provides an appropriate bias, and scales and converts the current flow into suitable units, using techniques that are well known in the art. For example, a measuring device such as a potentiostat can be used from which the measurement results can be read directly. In this respect, the embodiment of FIG. 4 operates in a manner similar to that described in conjunction with the embodiment of FIG. 2.

It should be noted that the embodiment of FIG. 4 is distinguished from the previously described embodiments not only by the fact that it is extremely miniaturized, but also by the fact that it must be removed in order to be refilled. Thus, in order to take advantage of the reusable aspect of this sensor, the same is removed, is disassembled and cleaned, and is then partially reassembled and refilled, all outside of the body or other tissue in which it is to be implanted.

Indications from tests employing apparatus constructed substantially in accordance with a FIG. 4 type embodiment of the present invention shows sustained responsiveness of the sensor to variations in glucose over a continuous period of at least 30 days. This indicates that the use of bulk amounts of immobilized and/or cross linked enzyme greatly extends the life of the sensor and thus extends the period of use before it is necessary to remove the sensor, disassemble it, clean it, partially reassemble it and refill it. After the sensor is partially reassembled and refilled, assembly is completed by attaching the membrane 4, for example by gluing it to the cathode or body 2 of the needle, or by placing an O-ring around the membrane, especially in the embodiment illustrated in FIG. 4. It is also possible to dip the needle into membrane material, such as polyurethane, cellulose acetate, or other polymers.

The reusable glucose sensor of the present invention provides several important advantages; long operational life because large quantities of active enzyme are immobilized on the very large surface area of fine particles; the fine particles carrying the enzyme are a three-dimensional system; the glucose can diffuse through in a fluid state to reach active enzyme; the total available three-dimensional volume of active enzyme is far greater than that which can be obtained with any known two-dimensional technique, such as enzymes immobilized on planar surface such as membranes, rods, etc. Further advantages include continuous monitoring of glucose concentration, a long lifetime provided by the ability to remove, disassemble, clean, reassemble and refill the sensor, small applied bias voltage and immobilization of enzymes on bulk particulate matter enabling efficient reaction with glucose and accurate measurement of glucose levels.

The reusable, miniature, implantable electrochemical sensor of the present invention constructed in conformity with the embodiment shown in FIG. 4 provides a construction whereby the useful life of the sensor is prolonged, and the performance thereof is stabilized. Such a sensor can, for example, be utilized to measure a specific chemical component in an industrial process, including but not limited to the food processing industry, the pharmaceutical industry, etc., with the specific chemical component being a component of the process which it is desired to monitor or measure. The inventive sensor can also be utilized to measure a specific chemical component in fluids used in clinical laboratories, medical offices and facilities, and research laboratories, with the specific chemical component being a component of the fluid which it is desired to monitor or measure.

While the invention has been described with respect to detection and measurement of glucose levels in bodily fluids, it should be understood that the invention applies also to other compounds or molecules including, but not limited to, amino acids, lactates, pyruvate, cholesterol, urea or the like which exist in bodily fluids which are substrates for different enzymes to undergo enzymatic conversion. Further, it should be understood that the invention applies also to any other chemical reaction which may be arranged to occur on a solid substrate (the fine particles), and produces a flow of electrons to produce a current, including but by no means limited to, for example, monoclonal antibodies. Also, the invention may be applied in a research laboratory, a clinical or hospital laboratory or industrial environment in connection with reactor vessels or other in vitro settings. Further, the invention may be applied to emergency medical treatment of trauma patients in the field.

Therefore, the present invention is, of course, in no way restricted to the specific disclosure of the specification and drawings, but also encompasses any modifications within the scope of the appended claims.

What I claim is:

1. A method of providing a reusable, miniature, implantable electrochemical sensor that employs an enzyme material for reaction with a specific chemical component of a first fluid that is initially located outside said sensor, with said enzyme material becoming spent or degraded after reaction, said method including the steps of:
   immobilizing said enzyme material on bulk particulate matter for reaction in said sensor with said specific component of said first fluid, said particulate matter, with said enzyme material immobilized thereon, being suspended in a second fluid;
   filling said sensor with said enzyme material immobilized on said particulate matter;
   implanting said sensor in an environment where said sensor comes into contact with said specific component of said first fluid;
   when said enzyme material is degraded; removing said sensor from said environment;
   subsequently removing from said sensor said particulate matter carrying said degraded enzyme material;
   refilling said sensor with fresh enzyme material immobilized on bulk particulate matter; and
   reimplanting said sensor.

2. A method according to claim 1, wherein said implanting steps comprise implanting said sensor in a living body, and wherein said specific chemical component of said first fluid is a bodily fluid component that is desired to be measured or monitored.

3. A method according to claim 1, wherein said bulk particulate matter comprises electrically conductive particles suspended in said second fluid.

4. A method according to claim 1, wherein said enzyme material is glucose oxidase, and said specific chemical component is glucose, and wherein said method further comprises the step of measuring said glucose by an electrochemical signal produced by said sensor, which is a hydrogen peroxide measuring sensor.

5. A method according to claim 1, wherein said enzyme material comprises glucose oxidase and catalase, and said specific chemical component is glucose, and wherein said method further comprises the step of measuring said glucose by an electrochemical signal produced by said sensor, which is an oxygen sensor.

6. A method according to claim 1, wherein said enzyme material is lactate enzymes, pyruvate enzymes, cholesterol enzymes, or urease, and said specific chemical component is lactate, pyruvate, cholesterol, or urea, and wherein said method further comprises the step of measuring said specific chemical component by an electrochemical signal produced by said sensor.

7. A method according to claim 1, wherein said bulk particulate matter comprises electrically conductive particles in bulk powder form suspended in a liquid.

8. A method according to claim 7, wherein said liquid is a gel.

9. A method according to claim 7, wherein said conductive particles comprise fine particles, the surface area of which are adapted to be activated physically or chemically to permit immobilization of said enzyme material thereon.

10. A method according to claim 1 for providing the reusable, miniature electrochemical sensor for an extended period of time in a living body for sensing at least one specific chemical component of bodily fluids, said method including the further steps of:
   providing a housing having at least one opening covered by membrane means that can be penetrated by said at least one specific chemical component, with said housing and said membrane means defining reaction chamber means for receiving said at least one specific chemical component, said reaction chamber means also containing said bulk particulate matter with said enzyme material immobilized thereon for chemically reacting with said at least one specific chemical component; said housing being removed from said living body for removing the degraded enzyme material therefrom and for refilling the sensor with the fresh enzyme material immobilized on bulk particulate matter, whereupon said housing is reimplanted in said living body; and
   disposing electrode means in said reaction chamber means for producing electrical signals corresponding to a chemical reaction between said enzyme material and said at least one specific chemical component.

* * * * *